US008252801B1

(12) United States Patent
Rueter et al.

(10) Patent No.: US 8,252,801 B1
(45) Date of Patent: Aug. 28, 2012

(54) TREATMENT OF SCHIZOPHRENIA AND RELATED DISORDERS

(75) Inventors: Lynne E. Rueter, Round Lake Beach, IL (US); Kaitlin E. Browman, Deerfield, IL (US); Jorge D. Brioni, Vernon Hills, IL (US); Marlon D. Cowart, Round Lake Beach, IL (US); Timothy A. Esbenshade, Schaumburg, IL (US); Gerard B. Fox, Barrington Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 33 days.

(21) Appl. No.: 12/793,434

(22) Filed: Jun. 3, 2010

Related U.S. Application Data

(60) Provisional application No. 61/183,813, filed on Jun. 3, 2009.

(51) Int. Cl.
*A01N 43/54* (2006.01)
*A61K 31/4965* (2006.01)

(52) U.S. Cl. .................................. 514/256; 514/255.01

(58) Field of Classification Search ................... 514/220
See application file for complete search history.

(56) References Cited

U.S. PATENT DOCUMENTS

| | | | |
|---|---|---|---|
| 3,539,573 | A | 11/1970 | Schmutz et al. |
| 4,710,500 | A | 12/1987 | Perregaard |
| 4,804,663 | A | 2/1989 | Kennis et al. |
| 4,831,031 | A | 5/1989 | Lowe |
| 4,879,288 | A | 11/1989 | Warawa et al. |
| 5,112,838 | A | 5/1992 | Perregaard et al. |
| 5,229,382 | A | 7/1993 | Chakrabarti et al. |
| 5,238,945 | A | 8/1993 | Perregaard et al. |
| 5,312,925 | A | 5/1994 | Allen et al. |
| 2007/0232612 | A1 | 10/2007 | Cowart et al. |

OTHER PUBLICATIONS

Fox et al. Pharmacological Properties of ABT-239 [4-(2-{2-[(2R)-2-Methylpyrrolidinyl]ethyl}-benzofuran-5-yl)benzonitrile]: II. Neurophysiological Characterization and Broad Preclinical Efficacy in Cognition and Schizophrenia of a Potent and Selective Histamine H3 Receptor Antagonist, The Journal of Pharmaceutical and Experimental Therapeutics, 313, 2005.*
Ananth, J., et al., "Side Effects of Atypical Antipsychotic Drugs," Current Pharmaceutical Design, 2004, vol. 10 (18), pp. 2219-2229.
Beasley, C., et al., "Olanzapine versus Placebo and Haloperidol Acute Phase Results of the North American Double-Blind Olanzapine Trial," Neuropsychopharmacology, 1996, vol. 14 (2), pp. 111-123.
Blin, O., "A Comparative Review of New Antipsychotics," Canadian Journal of Psychiatry, 1999, vol. 44 (3), pp. 235-244.
Cross. L, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Davis, J., et al., "Dose Response and Dose Equivalence of Antipsychotics," Journal of Clinical Psychopharmacology, 2004, vol. 24 (2), pp. 192-208.
Diagnostic and Statistical Manual of Mental Disorders, 4th edition, 2002, pp. 429-484.
Diagnostic Statistical Manual of Mental Disorders, 4th Edition, 2002, pp. 345-428.
Diagnostic Statistical Manual of Mental Disorders: Schizophrenia and other Psychotic Disorders, 4th Edition, American Psychiatric Association, 2002, pp. 297-343.
DSM-IV Diagnostic and Statistical Manual of Mental Disorders, 4th Edition, 2000, Table of Contents.
Furniss, B., et al., Vogel's Textbook of Practical Organic Chemistry, 5th Edition, Longman Scientific & Technical, 1989, Table of Contents.
Kane, J., et al., "Clozapine in Treatment-Resistant Schizophrenics," Psychopharmacology Bull, vol. 24, pp. 62-67, 1988.
Kapur, S., et al., "Atypical Antipsychotics: New Directions and New Challenges in the Treatment of Schizophrenia," Annual Review of Medicine, 2001, vol. 52, pp. 503-517.
Kapur, S., et al., "Relationship Between Dopamine D2 Occupancy Clinical Response, and Side Effects: A Double-Blind PET Study of First-Episode Schizophrenia," The American Journal of Psychiatry, 2000, vol. 157 (4), pp. 514-520.
Kinon, B., et al., "Dose Response and Atypical Antipsychotics in Schizophrenia," Central Nervous System Drugs, 2004, vol. 18 (9), pp. 597-616.
Kulisevsky, J., et al., "Antipsicoticos y efectos extrapiramidales," Neurologia, 2003, vol. 18 (5), pp. 262-268.
McEvoy, "Drug Information 2000", 2000, pp. 2125, 2135, 2142.
Naber, D., et al., "Aripiprazole: a new atypical antipsychotic with a different pharmacological mechanism," Progress in Neuro-Psychopharmacology & Biological Psychiatry, 2004, vol. 28 (8), pp. 1213-1219.
Olivier, B., et al., "The DBA/2J strain and prepulse inhibition of startle: a model system to test antipsychotics," Psychopharmacology, 2001, vol. 156 (2-3), pp. 284-290.
Ouagazzal, M., "Drug-induced potentiation of prepulse inhibition of acoustic startle reflex in mice: a model for detecting antipsychotic activity," Psychopharmacology (Berl), vol. 156 (2-3), pp. 273-283, 2001.
Poste, G., et al., "Lipid Vesicles as Carriers for Introducing Biologically Active Materials into Cells," Methods in Cell Biology, 1976, vol. 14, pp. 33-71.
"Practice Guidelines for the Treatment of Psychiatric Disorders Compendium 2002", American Psychiatric Assoc, 2002, Table of Contents.
Simosky, J., et al., "Clozapine improves deficient inhibitory auditory processing in DBA/2 mice, via a nicotinic cholinergic mechanism," Psychopharmacology, 2003, vol. 165 (4), pp. 386-396.
Tarsy, D., et al., "Effects of Newer Antipsychotics on Extrapyramidal Function," Central Nervous System Drugs, 2002, vol. 16 (1), pp. 23-45.

* cited by examiner

*Primary Examiner* — Sreeni Padmanabhan
*Assistant Examiner* — Timothy E Betton
(74) *Attorney, Agent, or Firm* — Lisa V. Mueller; Michael Best & Friedrich LLP (57) ABSTRACT

The invention relates to a method of administering histamine $H_3$ antagonist and an antipsychotic therapeutic agent, compositions comprising a histamine $H_3$ antagonist and an antipsychotic therapeutic agent, and a related article of manufacture.

7 Claims, 3 Drawing Sheets

Figure 2

Effect of Compound A on a subefficacious dose of risperidone in PPI in DBA2/J mice

Figure 3

TREATMENT OF SCHIZOPHRENIA AND RELATED DISORDERS

BACKGROUND OF THE INVENTION

This application claims the benefit of U.S. Provisional Patent Application No. 61/183,813, filed on Jun. 3, 2009, which is herein incorporated by reference in its entirety.

TECHNICAL FIELD

The invention relates to a composition comprising a method of administering histamine $H_3$ antagonist and an atypical antipsychotic, compositions comprising a histamine $H_3$ antagonist and an atypical antipsychotic, and a related article of manufacture.

DESCRIPTION OF RELATED TECHNOLOGY

Psychotic conditions such as schizophrenia and related disorders, for example schizoaffective disorder, are complex and heterogeneous diseases of uncertain etiology. With a worldwide prevalence of approximately one percent to two percent of the population, schizophrenia has serious social and economic consequences.

Schizophrenia itself is characterized by fundamental distortions in realms of thinking and perception, cognition and the experience of emotions. With a typical onset in late adolescence or early adulthood, it is a chronic lifelong illness with periods of frank psychotic features alternating with periods of residual symptoms and incomplete social recovery. Schizophrenia requires medical intervention in virtually all cases. Approximately 60% to 70% of schizophrenic patients never marry and the unemployment rate among schizophrenic patients is greater than 70%. Such statistics suggest that schizophrenic patients do not adequately function in society.

Symptoms of schizophrenia are subdivided into three major clusters: positive, negative, and cognitive. Positive (psychotic) symptoms, consist of delusions (false beliefs that cannot be corrected by reason), hallucinations (usually nonexistent voices), disorganized speech, and grossly disorganized behavior. Negative symptoms are described as affective flattening, alogia (speechlessness caused by mental confusion), avolition (lack of motivation to pursue a goal), and anhedonia (inability to experience pleasure). Cognitive deficits include impairments of working memory, attention, verbal reproduction, and executive function. Furthermore, a variety of associative features and mental disorders include poor insight, depersonalization, derealization, depression, anxiety, and substance abuse disorders. Finally, schizophrenia patients have a markedly increased risk of suicide rate with 20% to 40% attempting suicide at least once in their lifetime, and 10% of patients successively committing suicide. (DSM-IV Diagnostic and Statistical Manual of Mental Disorders, 4th edition, American Psychiatric Assoc., Washington, D.C., 2000).

The current standard of treatment for schizophrenia is the atypical antipsychotics, such as clozapine, risperidone, olanzapine, and sertindol, although there is still significant use of typical antipsychotics throughout the world. Typical antipsychotic drugs (phenothiazines, butryophenones, and thioxanthenes), which are also referred to as conventional, standard, classical, or first generation antipsychotic drugs, have until recently, been the core treatment of schizophrenia.

A limitation of treatment with the typical antipsychotics is the induction of extrapyramidal side effects (EPS). EPS include Parkinsonism, dystonia, akathisia and neuroleptic malignant syndrome as well as the irreversible movement disorder called tardive dyskinesia. Severe akathisia can cause patients to feel anxious or irritable and can result in aggressive or suicidal acts. The most troublesome neurological side effect, tardive dyskinesia, can be irreversible, the risk of which has been a major rationale for preference of atypical over typical drugs. The occurrence of EPS is dose dependent and occurs in up to 60% of patients treated with typical antipsychotics. In practice, clinicians titrate the dose for each patient in order to achieve the greatest efficacy with a manageable level of side effects. (Kinon et al, CNS Drugs, 2004, 18:597-616; Tarsy et al, CNS Drugs, 2002, 16:23-45; Kulisevsky and Otermin, Neurologia, 2003, 18:262-268). Thus, potential efficacy of the typical antipsychotic agent is limited by the narrow therapeutic window. Atypical antipsychotics typically are drugs that have at least equal antipsychotic efficacy and produce fewer discomforting acute and long-term adverse effects. These medications are generally accepted to be as effective in controlling positive symptoms as typical agents, and they may be more effective in the treatment of other aspects of the disorder (e.g. control of negative symptoms and cognitive deficits). Some of the newer atypical antipsychotics have a reduced liability, i.e. a greater therapeutic window in which to titrate efficacy, compared to typical antipsychotics. For example, atypical antipsychotics have a decreased risk of EPS induction as compared to the typical antipsychotics; however, such atypical antipsychotics can still induce EPS in greater than 30% of patients. Clozapine is an exception in that it produces few extrapyramidal side effects; however, this atypical neuroleptic is associated with agranulocytosis, a rare blood dyscrasia, which also limits its use.

In addition to EPS, currently available antipsychotics produce other side effects that limit their usefulness, the physician's ability to titrate to the optimal dose necessary to control the symptom clusters of the disorder, or both. These include secondary negative symptoms such as adverse cardiovascular effects, somnolence, weight gain, metabolic syndrome, and diabetes.

The adverse effects associated with the antipsychotics can lead to treatment noncompliance or treatment termination and, as such, increase the rate of relapse and rehospitalization during the course of the chronic illness. (Practice Guidelines for the Treatment of Psychiatric Disorders Compendium 2002, American Psychiatric Assoc., Washington, D.C., 2002; Kapur and Remington, Ann. Rev. Med, 2001, 52:503-517). As a result of the limited efficacy and the side effects, lack of patient compliance in taking medications is a serious problem in the treatment of schizophrenia. More than 40% of schizophrenic patients fail to take their medication as prescribed.

With the exception of tardive dyskinesia, EPS can be resolved by discontinuing treatment with the medication. However, discontinuing treatment puts the patient at risk of schizophrenia symptom relapse.

Accordingly, successful treatment using currently available antipsychotics is limited by the wide range of side effects associated with their use, albeit to differing degrees. CNS diseases such as psychotic disorders are an unmet medical need, and the methods and possibilities for treatments of such indications are insufficient. In light of the significance of psychotic disorders and the limitations in their treatment, it would be beneficial to identify new methods of treating such psychotic disorders, particularly in a manner that reduces the risk of EPS.

SUMMARY OF THE INVENTION

The present invention relates to treatment of individuals having psychotic disorders and related conditions with an antipsychotic drug and with a histamine $H_3$ receptor antagonist. The present invention provides for therapy of a patient having a psychotic disorder using an antipsychotic therapeutic agent with a histamine $H_3$ receptor antagonist. The therapy can involve administering a histamine $H_3$ antagonist and an antipsychotic therapeutic agent to a patient in need of treatment for a psychotic disorder, and particularly schizophrenia or schizophrenia-related disorders. The treatment also relates to a combination suitable for treating a psychotic condition. The method for treatment and the combination can be synergistic or additive in effect and will be beneficial for the treatment of psychotic disorders, especially in humans. Such combination reduces a patient's exposure to EPS and can provide a beneficial alternative to current treatments.

In one embodiment, the present invention relates to a method for treating or preventing a psychotic condition in a patient. In the method, the steps include, but are not limited to, (i) administering an antipsychotic therapeutic agent to a patient; and (ii) administering a histamine $H_3$ receptor antagonist to a patient; to treat symptoms of a psychotic condition. The histamine $H_3$ receptor antagonist can be administered to a patient receives or will receive therapy with an antipsychotic therapeutic agent, and particularly, an atypical antipsychotic. The antipsychotic therapeutic agent can be administered in an efficacious or subefficacious dose. A benefit of the invention is that administering a histamine $H_3$ antagonist to a patient in need of therapy for a psychotic condition, for example schizophrenia or schizophrenia-related conditions, for example, cognitive deficits of schizophrenia, allows for improved efficacy of the antipsychotic medication. Such effect can be useful for reducing the amount of antipsychotic therapeutic agent in a manner that the patient can receive the full benefit of treatment while being administered only a subefficacious dose of the antipsychotic therapeutic agent.

In another embodiment, the present invention relates to a composition comprising (i) an antipsychotic drug; and (ii) a histamine $H_3$ receptor antagonist, in admixture with at least one pharmaceutically acceptable excipient. One benefit of the present invention is a composition wherein the amounts of (i) and (ii) are together effective in treating a psychotic disorder, particularly with less EPS. However, a composition wherein (i) and (ii) are each present in an effective amount also is contemplated. The antipsychotic therapeutic agent can be a neuroleptic dopamine receptor antagonist or any other typical or atypical antipsychotic useful for treatment of schizophrenia or other psychotic related disorders.

Yet another embodiment relates to an article of manufacture, having (i) a first pharmaceutical dosage form with at least one antipsychotic; (ii) a second pharmaceutical dosage form with at least one histamine $H_3$ receptor antagonist; and wherein the article contains first and second pharmaceutical dosage forms.

The embodiments of the present invention, how to prepare them, and how to use them are further described herein.

DETAILED DESCRIPTION OF THE INVENTION

Histamine $H_3$ Receptor Antagonists

Histamine $H_3$ receptor antagonists of various structural classes have been identified. Histamine $H_3$ receptor antagonists have been identified as useful for treating various conditions. In particular, the invention relates to the use of histamine $H_3$ antagonists for treating psychotic disorders, as later defined herein, which can include, but are not limited to schizophrenia, schizophreniform disorder, schizoaffective disorder, and related aspects of schizophrenia, for example, cognitive deficits of schizophrenia. Many histamine $H_3$ receptor antagonists are reported in the literature.

Suitable histamine $H_3$ antagonists are, for example, compounds of formula:

(I)

or a pharmaceutically acceptable salt thereof, wherein:

$R_1$ is alkyl, $C_3$-$C_5$ cycloalkyl, or ($C_3$-$C_5$ cycloalkyl)methyl;

$R_{2a}$, $R_{2b}$, $R_{2c}$, $R_{2d}$, $R_{2e}$, and $R_{2f}$ each are independently hydrogen, methyl, or fluoromethyl;

$R_{3a}$, $R_{3b}$, $R_{3c}$, and $R_{3d}$ are each independently hydrogen, alkyl, fluoroalkyl, fluoroalkoxy, alkoxy, thioalkoxy, halogen, or nitrile, with the proviso that when one or more of $R_{3a}$, $R_{3b}$, $R_{3c}$, and $R_{3d}$ are alkyl, then at least one of $R_{3a}$, $R_{3b}$, $R_{3c}$, and $R_{3d}$ is fluoroalkyl, fluoroalkoxy, alkoxy, thioalkoxy, halogen, or nitrile;

$L_1$ is a bond, oxygen, sulfur, carbonyl, alkylene, alkylcarbonyl, alkylamino, —C(=N—Oalkyl)-, $NR_4$, —C(=O)$NR_4$—, or —$NR_4$C(=O)—;

$L_2$ is a bond, oxygen, sulfur, carbonyl, alkylene, alkylcarbonyl, alkylamino, —C(=N-Oalkyl)-, $NR_5$, —C(=O)$NR_5$—, or —$NR_5$C(=O)—, $Cy_1$ is aryl, cycloalkyl, cycloalkenyl, heteroaryl, or heterocycle;

$Cy_2$ is aryl, cycloalkyl, cycloalkenyl, heteroaryl or heterocycle, wherein the heteroaryl or heterocycle moiety has 1, 2, or 3 heteroatoms selected from nitrogen, oxygen, and sulfur, provided that at least one heteroatom is nitrogen; and $R_4$ and $R_5$ at each occurrence is hydrogen or alkyl;

provided that Cy$_2$ is not

More particular compounds of formula (I) are those compounds wherein L$_1$ is a bond; L$_2$ is a bond; R$_{3a}$, R$_{3b}$, R$_{3c}$, and R$_{3d}$ are all hydrogen; Cy$_1$ is phenyl, and Cy$_2$ is aryl, cycloalkyl, cycloalkenyl, heteroaryl or heterocycle, wherein the heteroaryl or heterocycle moiety has 1, 2, or 3 heteroatoms selected from nitrogen, oxygen, and sulfur, provided that at least one heteroatom is nitrogen. In particular, such compounds of formula (I) are preferred wherein Cy$_2$ represents pyridazinone.

Such compounds, salts, and method for preparing them are described in U.S. Patent Publication No. 2007/0232612, published Oct. 4, 2007, and its related applications. Contents of U.S. Patent Publication No. 2007/0232612 and its related application are herein incorporated by reference. Compounds generally and specifically, as well as the salts thereof, useful in the invention are described in U.S. Patent Publication No. 2007/0232612A1, published Oct. 4, 2007. One specific embodiment is 2-{4'-[(3aR,6aR)-5-methylhexahydropyrrolo [3,4-b]pyrrol-1(2H)-yl]-1,1'-biphenyl-4-yl}pyridazin-3 (2H)-one. Another specific embodiment is 2-{5-[4-((3aR, 6aR)-5-methyl-hexahydro-pyrrolo[3,4-b]pyrrol-1-yl)-phenyl]-pyridin-2-yl}-2H-pyridazin-3-one.

DEFINITION OF TERMS

Unless otherwise defined, terms as used in the specification refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —$NH_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_7R_8$, ($NR_7R_8$)carbonyl, —$SO_2N(R_9)(R_{10})$, and $N(R_9)SO_2(R_{10})$, wherein $R_7$, $R_8$ and $R_9$ are independently selected from the group hydrogen, $C_{1-4}$ alkyl, $C_3$-$C_4$ cycloalkyl, and aryl, and $R_{10}$ is selected from the group $C_{1-4}$ alkyl, $C_3$-$C_4$ cycloalkyl, and aryl. Where the aryl group is a phenyl group, the number of substituents is 0, 1, 2, 3, 4, or 5. Where the aryl group is a bicyclic aryl, the number of substituents is 0, 1, 2, 3, 4, 5, 6, 7, 8, or 9. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —$CO_2H$ group.

The term "cyano" as used herein means a —CN group, attached to the parent molecular moiety through the carbon.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 8 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, oxo, nitro, alkylthio, —$NR_7R_8$, ($NR_7R_8$)carbonyl, —$SO_2N(R_9)(R_{10})$, and —$N(R_9)SO_2(R_{10})$, wherein, $R_7$, $R_8$, $R_9$, and $R_{10}$ are defined herein.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. ($C_3$-$C_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through a alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle", as used herein, refers to non-aromatic cyclic groups that contain at least one heteroatom. Non-aromatic heterocycles are non-aromatic cyclic groups that contain at least one heteroatom; examples of non-aromatic heterocyclic groups or non-aromatic heterocycles are further defined below. Heterocyclic rings are connected to the parent molecular moiety through a carbon atom, or alternatively in the case of heterocyclic rings that contain a bivalent nitrogen atom having a free site for attachment, the heterocyclic ring may be connected to the parent molecular moiety though a nitrogen atom. Additionally, the heterocycles may be present as tautomers.

The term "heteroaryl", as used herein, refers to an aromatic ring containing one or more heteroatoms independently selected from nitrogen, oxygen, and sulfur. Such rings can be monocyclic or bicyclic as further described herein. Heteroaryl rings are connected to the parent molecular moiety, or to $L_1$ or $L_2$, wherein $L_1$ and $L_2$ are defined in formula (I), through a carbon or nitrogen atom.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contains 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and or one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring has been replaced with at least one heteroatom selected from oxygen, sulfur, and nitrogen. The bicyclic heteroaryl of the invention may be attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —$NR_7R_8$, ($NR_7R_8$)carbonyl, —$SO_2N(R_9)(R_{10})$, and —$N(R_9)SO_2(R_{10})$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring may contain zero, one, or two double bonds provided that the ring, when taken together with a substituent, does not tautomerize with a substituent to form an aromatic ring. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_7R_8$, ($NR_7R_8$)carbonyl, —$SO_2N(R_9)(R_{10})$, and —$N(R_9)SO_2(R_{10})$.

Additional examples of heterocycles include, but are not limited to, isoindoline-1,3-dione, (Z)-1H-benzo[e][1,4]diazepin-5(4H)-one, pyrimidine-2,4(1H,3H)-dione, benzo[d]thiazol-2(3H)-one, pyridin-4(1H)-one, imidazolidin-2-one, 1H-imidazol-2(3H)-one, pyridazin-3(2H)-one, tetrahydropyrimidin-2(1H)-one, and 1H-benzo[d]imidazol-2(3H)-one.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "$(NR_7R_8)$" as used herein means both $R_7$ and $R_8$ group, as defined herein, appended to the parent molecular moiety through a nitrogen atom. $R_7$ and $R_8$ are each independently selected from the group consisting of hydrogen, $C_{1-4}$ alkyl, $C_3$-$C_4$ cycloalkyl, and aryl.

The term "$(NR_7R_8)$alkyl" as used herein means an —$NR_7R_8$ group, as defined herein, appended to the parent molecular moiety through an alkyl group, as defined herein. Representative examples of $(NR_7R_8)$alkyl include, but are not limited to, 2-(methylamino)ethyl, 2-(dimethylamino)ethyl, 2-(amino)ethyl, 2-(ethylmethylamino)ethyl, and the like.

The term "$(NR_7R_8)$carbonyl" as used herein means an —$NR_7R_8$ group, as defined herein, appended to the parent molecular moiety through a carbonyl group, as defined herein. Representative examples of $(NR_7R_8)$carbonyl include, but are not limited to, aminocarbonyl, (methylamino)carbonyl, (dimethylamino)carbonyl, (ethylmethylamino)carbonyl, and the like.

The term "$(NR_7R_8)$sulfonyl" as used herein means a —$NR_7R_8$ group, as defined herein, appended to the parent molecular moiety through a sulfonyl group, as defined herein. Representative examples of $(NR_7R_8)$sulfonyl include, but are not limited to, aminosulfonyl, (methylamino)sulfonyl, (dimethylamino)sulfonyl and (ethylmethylamino)sulfonyl.

The term "—$N(R_9)SO_2(R_{10})$" as used herein means an amino group attached to the parent moiety to which is further appended with an $R_9$ group as defined herein, and a $SO_2$ group to which is appended an $(R_{10})$ group as defined herein. $R_9$ is selected from the group consisting of hydrogen, $C_{1-4}$ alkyl, $C_3$-$C_4$ cycloalkyl, and aryl, and $R_{10}$ is selected from the group consisting of $C_{1-4}$ alkyl, $C_3$-$C_4$ cycloalkyl, and aryl. Representative examples of —$N(R_9)SO_2(R_{10})$ include, but are not limited to, N-methylmethanesulfonamide.

The term "—$SO_2N(R_9)(R_{10})$" as used herein means a $N(R_9)(R_{10})$ group attached to a $SO_2$ group, wherein $R_9$ and $R_{10}$ are as defined —$N(R_9)SO_2(R_{10})$, appended to the parent moiety through the sulfonyl group. Representative examples of —$SO_2N(R_9)(R_{10})$ include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

The compounds of the invention can be used in the form of pharmaceutically acceptable salts derived from inorganic or organic acids. The term "pharmaceutically acceptable salts", as used herein, refer to acid addition salts, carboxylate salts, amino acid addition salts, and zwitterion salts of compounds of formulae (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable acid. Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, proprionic, hydrobromic, glucuronic, methanesulfonic, ethanesulfonic, naphthylene sulfonic, lactic, fumaric, oxalic, and succinic acid. Representative acid addition salts include, but are not limited to, ascorbic acid, (D)-tartaric acid, (L)-tartaric acid, phosphoric acid, salicylic acid, sulfuric acid, trifluoroacetic acid, and hydrochloric acid.

The aforementioned histamine $H_3$ antagonist antagonists may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Histamine $H_3$ receptor antagonists may exist as cis or trans isomers, wherein substituents on a ring may attached in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Compositions comprising a therapeutically effective amount of a compound of formulae (I) in combination with a pharmaceutically acceptable carrier also are suitable for the method. The compositions comprise the histamine $H_3$ receptor antagonist formulated together with one or more non-toxic pharmaceutically acceptable carriers. The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Antipsychotic Therapeutic Agent

Antipsychotic therapeutic agents are pharmaceutical actives that have been commonly used in the treatment of schizophrenia and other conditions related to psychosis dysfunction. Many antipsychotic therapeutic agents, for example typical, or classical, antipsychotics and atypical antipsychotics are well known to those skilled in the art.

Typical antipsychotics demonstrate antagonism at the dopamine D2 receptors. Typical antipsychotics generally are classified into three groups according to their potency. For example, typical antipsychotics include high affinity agents, such as haloperidol and fluphenazine; intermediate potency agents, such as loxapine; and low potency agents, such as chlorpromazine. Typical antipsychotics are associated with efficacy against positive symptoms but with significant incidence of side effects including EPS and sedation. Atypical antipsychotics demonstrate a high level of affinity for the 5HT2 receptor and functions as an antagonist of serotonin at that receptor. While the exact mechanism by which these compounds exert their antipsychotic effect is still under review, it is believed that at least part of their efficacy stems from their ability to modulate serotonergic transmission within the CNS. While atypical antipsychotics often have affinity for dopaminergic receptors within the CNS, they are much less potent dopaminergic antagonists than classical antipsychotics, such as chlorpromazine, haloperidol, and others. A detailed discussion of these compounds and their mechanism of action can be found in Blin, Comparative Review of New Antipsychotics, Can J Psychiatry, Vol 44, 235-242 April 1999. In addition to their differing mechanism of action, atypical antipsychotics can be differentiated from classical antipsychotics based upon their side effect profile. Atypical antipsychotics are associated with a significantly reduced incidence of acute extrapyramidal symptoms, especially dystonias, when compared to a typical antipsychotic such as haloperidol. (Beasley, et al., Neuropsychopharmacology, 14(2), 111-123, (1996); Ananth J, et al., Curr. Pharm. Des. 10(18):2219-29 (2004)).

Typical antipsychotic agents can include compounds that are D2 antagonists, for example, phenthiazines, butryrophenones, and thiozanthenes. Examples of such classes of compounds include, but are not limited to, fluphenazine, chlorpromazine, haloperidol, and loxapine.

Atypical antipsychotic agents can include compounds that are mixed antagonists that usually, but are not limited to, demonstrate D2 and 5-HT2 antagonism. Examples include clozapine, risperidone, olanzapine, quetiapine, ziprasidone, and arpiprazole. Adjunctive antipsychotic agents can include compounds that are antiepileptics, antidepressants, or anticholinergics. Examples of such classes of compounds include, but are not limited to, beta blockers, antioxidants, benzodiazepines, L-dopa, H2 antagonists, and 5HT1A agonists.

Any other compound having a pharmacological profile or clinical benefit analogous to the compounds described above or other compounds emerging via targeting subtypes or subunits of receptors, ion channels, enzymes, or other mechanisms, should also be considered to be encompassed by the term antipsychotic even if that compound is discovered after the filing of this application.

Examples of suitable typical antipsychotics include, but are not limited to the following compounds, below.

Haloperidol (Haldol), 4-(4-chlorophenyl)-1-[4-(4-fluorophenyl)-4-oxobutyl]-4 piperidinyl, is available in oral (solution, tablets) or in a parenteral form from Ortho McNeil Pharmaceuticals. Haloperidol decanoate, which is administered intramuscularly as a depot preparation, is an alternative for long-term therapy.

Chlorpromazine (Thorazine, Largactil), 10-(3-dimethylaminopropyl)-2-chlorphenothiazine, is available in oral or in parenteral form from GlaxoSmithKline and others.

Fluphenazine (Modecate, Permitil, Prolixin), 4-[3-[2-(trifluor-omethyl)phenothiazin-10H-yl]propyl]-1-piperazineethanol, is available in oral or in parenteral form from Boehringer Ingeheim and others. Fluphenazine deconoate, which is administered intramuscularly as a depot preparation, is an alternative for long-term therapy. Examples of suitable atypical antipsychotics include, but are not limited to, the following compounds, below.

Risperidone, 3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one, and its use in the treatment of psychotic diseases are described in U.S. Pat. No. 4,804,663. Risperidone is available commercially from Janssen. A detailed discussion of risperidone, its dosing schedule, potential side effects, and other information, may be found in AHFS, Drug Information 2000, page 2142, which is published by the American Society of Hospital Pharmacists (editor-McEvoy).

Olanzapine, 2-methyl-4-(4-methyl-1-piperazinyl)-10H-thieno[2,3-b][1,5]benzodiazepine, is a known compound and is described in U.S. Pat. No. 5,229,382 as being useful for the treatment of schizophrenia, schizophreniform disorder, acute mania, mild anxiety states, and psychosis. U.S. Pat. No. 5,229,382. Olanzapine is available commercially from Eli Lilly. A detailed discussion of olanzapine, its dosing schedule, potential side effects, etc., may be found in AHFS, Drug Information 2000, page 2135, which is published by the American Society of Hospital Pharmacists (editor-McEvoy).

Clozapine, 8-chloro-11-(4-methyl-1-piperazinyl)-5H-dibenzo[b,e][1,4]diazepine, is described in U.S. Pat. No. 3,539,573. Clinical efficacy in the treatment of schizophrenia is described by Hanes et al, Psychopharmacol. Bull., 24, 62 (1988). Clozapine is available commercially from Novartis. A detailed discussion of clozapine, its dosing schedule, potential side effects, etc., may be found in AHFS, Drug Information 2000, page 2125, which is published by the American Society of Hospital Pharmacists (editor-McEvoy).

Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288. Quetiapine is typically administered as its (E)-2-butenedioate (2:1) salt. It is available commercially from AstraZeneca. A detailed discussion of quetiapine, its dosing schedule, potential side effects, and other aspects of the treatment, may be found in AHFS, Drug Information 2000, page 2142, which is published by the Americal Society of Hospital Pharmacists (editor-McEvoy).

Ziprasidone, 5-[2-[4-(1,2-benzoisothiazol-3-yl)-1-piperazinyl]ethyl]-6-chloro-1,3-dihydro-2H-indol-2-one, is typically administered as the hydrochloride monohydrate. It is commercially available from Pfizer. The compound is described in U.S. Pat. Nos. 4,831,031 and 5,312,925. Its activity in assays which demonstrate utility in the treatment of schizophrenia are described in U.S. Pat. No. 4,831,031. U.S. Pat. Nos. 4,831,031 and 5,312,925.

Aripiprazole (Abilify) is an atypical antipsychotic drug that has been recently introduced for clinical use in the treatment of schizophrenia. Additional information can be obtained from Bristol-Myers Squibb. Naber, et al., in Prog Neuropsychopharmacol Biol Psychiatry. 2004 Dec. 28(8): 1213-9, evaluated the antipsychotic effect of arpiprazole.

Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 4,710,500; 5,112,838; and 5,238,945.

Zotepine, 2-{(8-chlorodibenzo[b,f]thiepine-10-yl)oxy]-N,N-dimethylethylamine, is available commercially from Knoll under the tradename Zoleptil®. It is approved for use as an antipsychotic in Japan and Germany.

Perospirone is marketed in Japan for schizophrenia by Yoshitomi. Further information regarding the compound can be obtained from Sumitomo Pharmaceutical, of Japan.

Aberrant sensory gating and altered neurotransmission mechanisms are recognized as etiological factors in schizophrenia psychopathology. One well-known aspect is that schizophrenic patients generally demonstrate the lack of an ability to gate, or sort sensory activity, appropriately.

Accordingly, some medicines still in the early stages of development that act on the 5HT and dopamine receptors are believed to be suitable for the present invention as well. For example, EMR-62218, under investigation by Merck Pharmaceuticals, and eplivanserin (Sanofi-Synthélabo), are reported to be selective inhibitors of the 5HT2A receptor with no dopamine blockade. SSR-181507 (Sanofi-Synthélabo) is reported to be a mixed dopamine D2/5HT2A antagonist, while SB271046 (GlaxoSmithKline) is an antagonist of the 5HT6 receptor that have progressed into clinical trials. PNU-177864 (Pfizer) is reported to be a highly selective partial blocker of the dopamine D3 receptor. SR-125047 (Sanofi-Synthélabo) is reported to be a compound that modulates a brain site called the central sigma receptor, to which haloperidol has also been shown to bind.

Rimonabant (formerly SR-141716), a blocker of the cannabinoid receptor, also may be suitable.

Neurokinin-3 antagonists, such as osanetant and talnetant (SB223412), currently are under investigation in clinical trials. Neurokinins are chemical compounds called peptides found in the substantia nigra and striatum regions of the brain. Neurokinins are involved in movement control, which are believed to be relevant to some of the side effects of neuroleptic medicines. Accordingly, it is contemplated that the combination of a histamine $H_3$ receptor antagonist with a neurokinin-3 antagonist also will demonstrate useful adjuvant therapy in similar manner as with antipsychotic previously described.

An entirely different approach to schizophrenia is the testing of inhibitors of a brain enzyme responsible for the breakdown of polyunsaturated fatty acids in cell membranes. A compound of this type, LAX-101d (Laxdale Pharmaceuticals) has emerged into clinical trials. It is contemplated that such histamine $H_3$ receptor antagonist can influence neuronal activity and, in combinations with such mechanisms that influence membrane properties, could enhance effectiveness of compounds. Further information regarding how to prepare the compounds and relevant dosing information can be obtained from the respective manufacturers as clinical trials advance.

Administering the Histamine $H_3$ Receptor Antagonist

Histamine $H_3$ receptor antagonists are compounds which block activation of the histamine $H_3$ receptor. The histamine $H_3$ receptor antagonist compounds and compositions of the invention can be used for treating and preventing schizophrenia and related disorders in a mammal. The compound, including salts thereof, or a composition can be administered for treatment of schizophrenia, schizophreniform disorder, schizoaffective disorder, or cognitive deficits of schizophrenia. The histamine-3 receptor antagonist can be administered, either alone or in combination with another active agent, for example, as part of a therapeutic regimen or in addition to an existing therapeutic regimen.

The pharmaceutical compositions can be formulated for oral administration in solid or liquid form, for parenteral intravenous, subcutaneous, intramuscular, intraperitoneal, intraarterial, or intradermal injection, for or for vaginal, nasal, topical, or rectal administration.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

The compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes may be used. Compositions in liposome form may contain, in addition to the compounds of the invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Dosage forms for topical administration of a compound for the treatment include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The pharmaceutical compositions can be administered to humans and other mammals by oral administration or by injection, including by intravenous, subcutaneous, intramuscular, intraperitoneal, intra-arterial, and intradermal injection. The pharmaceutical compositions can be administered to humans and other mammals topically (as by powders, lotions, ointments or drops applied to the skin), bucally, or inhaled, as an oral or nasal spray. The pharmaceutical compositions also can be administered to humans and other mammals intrarectally or intravaginally. The term "parenterally," as used herein, refers to modes of administration, which include intravenous, intramuscular, intraperitoneal, intrasternal, subcutaneous and intraarticular.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of formula (I) administered to a human or lower animal may range from about 0.0003 to about 30 mg/kg of body weight. For purposes of oral administration, more preferable doses can be in the range of from about 0.001 to about 0.1 mg/kg body weight. If desired, the effective daily dose can be divided into multiple doses for purposes of administration; consequently, single dose compositions may contain such amounts or submultiples thereof to make up the daily dose.

As a general guide, suitable unit doses for compounds of formula (I) in humans are from about 1 mg to about 15 mg for therapy in a patient in need of treatment for schizophrenia, including cognitive deficits of schizophrenia, schizophreniform disorder, schizoaffective disorders, and other related psychotic disorders. For example, 2-{4'-[(3aR,6aR)-5-methylhexahydropyrrolo[3,4-b]pyrrol-1(2H)-yl]-1,1'-biphenyl-4-yl}pyridazin-3(2H)-one may be administered in an amount of 1, 3, 6, 9, 12, or 15 milligrams daily in patients in need of treatment for schizophrenia, including patients receiving treatment with an atypical antipsychotic.

Optimal dosages to be administered may be readily determined by those skilled in the art, and will vary with the particular compound used, the mod of administration, the strength of the preparation, the mode of administration, and the advancement of the disease condition. In addition, factors associated with the particular patient being treated, including patient age, weight, diet, and time of administration can result in the need to adjust dosages.

Method of the Invention

As noted above, it has been discovered that psychotic conditions can be treated by concurrently administering to a patient (i.e. a human) in need thereof, an antipsychotic and a histamine $H_3$ receptor antagonist. It has been discovered that such use is especially beneficial in expanding the dosage range and reducing the incidence of EPS.

As used in this application, the term "treating" or "treated" refers to administering a compound to a subject with the purpose to cure, heal, alleviate, relieve, alter, remedy, ameliorate, improve, or affect a disease, the symptoms of the disease, or the predisposition toward the disease.

As used in this application, the term "concurrent administration" or "concurrently administering" refers to administering the histamine $H_3$ receptor antagonist to a patient, who has been prescribed (or has consumed) at least one antipsychotic, at an appropriate time so that the patient's symptoms may subside. This may mean simultaneous administration of the histamine $H_3$ receptor antagonist and the antipsychotic, or administration of the medications at different, but appropriate times. Establishing such a proper dosing schedule will be readily apparent to one skilled in the art, such as a psychiatrist, or other physician.

The dosage range at which the antipsychotic and the histamine $H_3$ receptor antagonist will be administered concurrently can vary widely. The specific dosage will be chosen by the patient's physician taking into account the particular antipsychotic chosen, the severity of the patient's illness, any other medical conditions or diseases the patient is suffering from, other drugs the patient is taking and their potential to cause an interaction or adverse event, the patient's previous response to antipsychotic medication, and other factors.

The antipsychotic and the histamine $H_3$ receptor antagonist should be administered concurrently in amounts that are effective to treat the patient's schizophrenia or related condition. In more general terms, one would choose a dosage of an antipsychotic and a dosage of the histamine $H_3$ receptor antagonist according to the spirit of the guidelines presented herein.

The antipsychotic therapy is carried out by administering an antipsychotic together with a histamine $H_3$ receptor antagonist in any manner which provides effective levels of the compounds in the body at the same time. Typically, the combination will be administered orally.

However, the invention is not limited to oral administration. The invention should be construed to cover any route of administration that is appropriate for the medications involved and for the patient. For example, transdermal administration may be very desirable for patients who are forgetful or petulant about taking oral medicine. Injections may be appropriate for patients refusing their medication. One of the drugs may be administered by one route, such as oral, and the others may be administered by the transdermal, percutaneous, intravenous, intramuscular, intranasal, or intrarectal route, in particular circumstances. The route of administration may be varied in any way, limited by the physical properties of the drugs and the convenience of the patient and the caregiver.

The following examples are being presented to further illustrate the invention. They should not be construed as limiting the invention in any manner. The dosage range of the currently available antipsychotics can be broad. Treatment-limiting side effects such as EPS are dose related, as previously described. Therefore, as an example, typical dose ranges for some commonly used antipsychotics are below. This list is not intended to be complete but is merely an illustration of current clinical usage and its correlation with EPS risk. Guidelines for current use of antipsychotic drugs, dose ranges, and their side effect profiles are shown below in Table 1.

TABLE 1

| Currently used Antipsychotic Drugs, Dose Ranges, and Side Effect Profiles | | | |
|---|---|---|---|
| Antipsychotic medication | Clinical Dose Range (common/ recommended dose (full reported range)) | EPS risk | Other Dose Related Side Effects |
| Haloperidol | 2-5 mg/kg per day (0.5 to 10 mg/kg per day) | ++++ | hyper-prolactinaemia; sexual dysfunction |
| Risperidone | 2-8 mg/kg per day | ++ (augmented risk | hyper-prolactinaemia; |

TABLE 1-continued

| Currently used Antipsychotic Drugs, Dose Ranges, and Side Effect Profiles | | | |
|---|---|---|---|
| Antipsychotic medication | Clinical Dose Range (common/ recommended dose (full reported range)) | EPS risk | Other Dose Related Side Effects |
| | (0.25 to 16 mg/kg per day) | >6 mg/kg/day) | sexual dysfunction |
| Olanzapine | 1-30 mg/kg per day (0.25 to 100 mg/kg per day) | + (augmented risk >7.5 mg/kg/day) | |
| Clozapine | 200-600 mg/kg per day (12.5 to 900 mg/kg per day) | +/− | seizures (risk of seizures augmented >600 mg/kg/day); somnolence; increased triodo-thyronine an thyroxine levels |
| Quetiapine | >500 mg/kg per day (150 to 750 mg/kg per day) | +/− | |
| Ziprasidone | 80-160 mg/kg per day (4-160 mg/kg per day) | ++ (augmented risk >80 mg/kg/day) | |
| Arpiprazole | 10-15 mg/kg day (10-20 mg/kg per day) | +/− | somnolence |

Table 1 references include Practice Guidelines for the Treatment of Psychiatric Disorders Compendium 2002, American Psychiatric Assoc., Washington, D.C., 2002; Kapur and Remington, Ann. Rev. Med, 2001, 52:503-517; Kinon et al, CNS Drugs, 2004, 18:597-616; Tarsy et al, CNS Drugs, 2002, 16:23-45; Kulisevsky and Otermin, Neurologia, 2003, 18:262-268; Davis and Chen; J Clin Psychopharmacol, 2004, 24, 192-208)

An agent that meaningfully enhances efficacy of antipsychotic agent without alone causing adverse effects (e.g. extrapyramidal effects) or exaggerating the side effect profile of the antipsychotic agent, such as a histamine $H_3$ receptor antagonist, should enhance the therapeutic window of the antipsychotic agent. There is no known prior knowledge for the use of histamine $H_3$ receptor antagonist as adjunctive therapy to increase the therapeutic window by enhancing alleviation of positive symptoms without exacerbating side effects. However, the ability of an adjunctive agent, i.e. histamine $H_3$ receptor antagonist to increase the potency and efficacy of an antipsychotic would potentially enhance the clinical utility of the antipsychotic by increasing the therapeutic window in which the clinician can titrate the dose. This would be relevant both for the typical antipsychotics that have the greatest EPS liability where the increased therapeutic window may be small but meaningful as well as for atypical antipsychotics that show EPS at higher doses where the increased therapeutic window could be expected to be substantially larger.

Accordingly, in the present invention, an antipsychotic is used with a histamine $H_3$ receptor antagonist, and can be administered at a lower dose, including a sub efficacious dose to have a better effect, and to eliminate or reduce the incidence of antipsychotic related side effects commonly encountered in the clinic. Examples of suitable dose range determinations for antipsychotic therapeutic agents are shown below in Table 2.

TABLE 2

Example Dose Range Determinations for Antipsychotics

| Antipsychotic Medication | Maximum Dose in Common Clinical Range | Optimal Dose and/or Minimally Effective Dose | Dose of Increased Side Effect Risk | Decrease in Common Dose to Meaningfully Impact Side Effects |
|---|---|---|---|---|
| Haloperidol | 5 mg/day | 2-5 mg/day | ≈3 mg (>78% $D_2$ occupancy increases risk for EPS) | 50% |
| Risperidone | 8 mg/day | 4-6 mg/day | ≧6 mg/day (EPS risk) | 25-50% |
| Olanzapine | 30 mg/day | 10-20 mg/day | | 33% |
| Clozapine | 600 mg/day | 300-400 mg/day | <300 mg/day (low risk for seizures) 300-599 mg/day (moderate risk for seizures) | 33-50% |
| Ziprasidone | 160 mg/day | 120 mg/day | >80 mg/day (EPS risk) | 25-50% |
| Aripiprazole | 20 mg/day | 15 mg/day | dose dependent somnolence | 25% |

References for Table 2: Practice Guidelines for the Treatment of Psychiatric Disorders Compendium 2002, American Psychiatric Assoc., Washington D.C., 2002; Kapur, et al., Am. J. Psychiatry (2000) vol. 157: 514-20.

To meaningfully reduce risk of dose dependent side effects associated with antipsychotics, when histamine $H_3$ receptor antagonist are added to the therapy, the doses of the antipsychotics would be reduced by about 25-50% and/or limited to about 25-50% of standard maximum doses used in common practice. For example, the dose can be reduced by at least about 25%, at least about 33%, or at least about 50%. At these doses, the patient would retain full antipsychotic efficacy against positive symptoms but at lower risk for side effects such as EPS.

The term "effective amount" as used herein refers to a sufficient amount of the individual compound to treat or prevent anxiety disorders, mood disorders, and psychotic disorders or the condition to be treated at a reasonable benefit/risk ratio in the judgment of the administering specialist applicable to any medical treatment.

The term "sub efficacious" as used herein, for example to refer to a "sub efficacious dose" or a "sub efficacious amount" refers to a dose or amount of the individual compound less than an amount for treating or preventing anxiety disorders, mood disorders, psychotic disorders or the condition to be treated at a reasonable benefit/risk ratio in the judgment of the administering specialist applicable to the medical treatment.

The term "maximally efficacious" as used herein, for example to refer to a "maximally efficacious dose" or a "maximally efficacious amount" refers to a dose or amount of the individual compound having the greatest effect for treating or preventing anxiety disorders, mood disorders, psychotic disorders or the condition to be treated at a reasonable benefit/risk ratio in the judgment of the administering specialist applicable to the medical treatment.

The specific effective dose level for any particular patient will depend upon a variety of factors including the disorder being treated and the severity of the disorder; activity of the specific compound employed; the specific composition employed; the age. However, some variation in dosage will necessarily occur depending upon the condition of the subject being treated. The person responsible for administration will, in any event, determine the appropriate dose for the individual subject.

The exact formulation, route of administration, and dosage can be chosen by the individual physician in view of the patient's condition. Dosage amount and interval can be adjusted individually to provide plasma levels of the active moiety which are sufficient to maintain therapeutic effects.

The following dosage amounts and other dosage amounts set forth elsewhere in this description and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject. All doses set forth herein, and throughout the appendant claims, if applicable, are daily doses.

The suitable amount of antipsychotic drug is based on recommended dose range, preferably at the low end, for example as illustrated in Table 2, and combined with an effective dose of the histamine $H_3$ receptor antagonist. The effective dose range of the histamine $H_3$ receptor antagonist will be adjusted to ensure efficacious plasma levels judged from clinical trials and can range depending on the duration of administration (once or twice daily or sustained release) of the product, as recommended by the manufacturer.

Formulations

The antipsychotic and histamine $H_3$ receptor antagonist compounds can be administered as a single pharmaceutical composition, or separately to achieve a concomitant or controlled effect. Such compositions may take any physical form that is suitable for pharmaceuticals. Pharmaceutical compositions suitable for oral administration are particularly preferred. Such pharmaceutical compositions contain an effective amount of each of the compounds, which effective amount is related to the daily dose of the compounds to be administered. Each dosage unit may contain the daily doses of all compounds, or may contain a fraction of the daily doses, such as one-third of the doses. Alternatively, each dosage unit may contain the entire dose of one of the compounds, and a fraction of the dose of the other compounds. In such case, the patient would daily take one of the combination dosage units, and one or more units containing only the other compounds. The amounts of each drug to be contained in each dosage unit depends on the identity of the drugs chosen for the therapy, and other factors such as the indication for which the antipsychotic therapy is being given.

The composition contains at least one pharmaceutically acceptable excipient, or inert ingredient. The inert ingredients and manner of formulating the pharmaceutical compositions are conventional, except for the presence of the combination of the present invention. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound, which provides the desired dose to the patient in need of such treatment. The specific combination of any antipsychotic and histamine $H_3$ receptor antagonist or compounds can be chosen and formulated solely for convenience and economy. Any of the combinations may be formulated in any desired form of composition. Some examples of compositions are described herein, followed by some typical formulations.

Capsules are prepared by mixing the compounds with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours, and similar edible powders.

If desired, the capsules can be formulated so that the contents are removed from the capsules prior to ingestion by the patient. The capsule contents may be diluted in foods, juices, or other substance, in order to simplify administration to those who have difficulty swallowing. Methods for manufacturing such a dosage form would be readily apparent to one skilled in the art.

The medications may also be formulated into liquids or syrups, as is known in the art, in order to simplify administration. The medication can be dissolved in or added to liquids, flavorants, antioxidants, stabilizers, or other inactive ingredients, as is known in the art. Such dosage forms have particular suitability with the elderly, such as dementia patients.

Tablets are prepared by direct compression, by wet granulation, or by dry granulation. Their formulations usually incorporate diluents, binders, lubricants, and disintegrators as well as the compound. Typical diluents include, for example, various types of starch, lactose, mannitol, kaolin, calcium phosphate or sulfate, inorganic salts such as sodium chloride, and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid, and hydrogenated vegetable oils.

Tablet disintegrators are substances, which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp, and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate, and hydroxypropyl methylcellulose acetate succinate.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches also are suitable for administering the combination. Typically transdermal patches comprise a resinous composition in which the drugs will dissolve, or partially dissolve, which is held in contact with the skin by a film which protects the composition. More complicated patch compositions are also in use, particularly those having a membrane pierced with innumerable pores through which the drugs are pumped by osmotic action.

Packaging

To enhance patient convenience, any antipsychotic and histamine $H_3$ receptor antagonist may be formulated into a single dosage form. Alternatively, separate dosage forms can be used, yet packaged in a single container for dispensing by the pharmacist, for example, as with a blister pack. Such packaging is typically designed to help a patient comply with a dosage regimen and to consume all of the required medication.

An article of manufacture, typically refers to the packaging, can comprise a first pharmaceutical dosage form with an antipsychotic and a second pharmaceutical dosage form with a histamine $H_3$ receptor antagonist. The article of manufacture can contain a first and second pharmaceutical dosage form in a single dosage form or as separate dosage forms.

Examples of such packaging are well known to those skilled in the pharmaceutical arts. For example, Pfizer distributes an antibiotic known as Zithromax®. Patients must consume 2 pills on the first day and one pill after that for 4 days in order to eradicate the infection. To allow a patient to comply with such a complicated schedule, Pfizer packages the medication in a blister pack that is commonly referred to as a Z-pack. Similar packages are used with steroids in which the dosage must be tapered. Birth control pills are another example of packaging pharmaceuticals to enhance convenience.

The antipsychotic and histamine $H_3$ receptor antagonist may be incorporated into such packaging to enhance patient convenience. If desired, such packaging may be used even if the antipsychotic and histamine $H_3$ receptor antagonist are in a single dosage form. The particulars of such packaging will be readily apparent to one skilled in the art.

As is well-known to those skilled in the art, the packaged pharmaceutical will include an insert. Such insert describes the drugs, their doses, possible side effects and indication. Thus, the present invention should be construed to include a package containing at least one antipsychotic compound in combination with at least one histamine $H_3$ receptor antagonist. The compounds may be in a single or separate dosage forms.

Psychotic Disorders

As noted above, the use of an antipsychotic therapeutic agent and a histamine $H_3$ receptor antagonist together will have efficacy in psychoses and other disorders or mental illnesses besides schizophrenia.

For example, schizophreniform is a condition exhibiting the same symptoms as schizophrenia, but is characterized by an acute onset with resolution in two weeks to six months. Often, schizophreniform is used to describe a patient's first schizophrenic episode. The patient presents with symptoms identical to those seen in the acute phase of schizophrenia, but the patient has no previous history of schizophrenia. Clinicians also refer to schizophreniform as "early schizophrenia". Treatment for schizophreniform disorder can be accomplished in the manner as previously described for the administration and formulation of the invention.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; brief psychotic disorder; shared psychotic disorder; psychotic disorder due to a general medical condition; substance-induced psychotic disorder, for example psychosis induced by alcohol, amphetamine, cannabis, cocaine, hallucinogens, inhalants, opioids, or phencyclidine; personality disorder of the paranoid type; personality disorder of the schizoid type; psychotic disorder not otherwise specified.

The meanings attributed to the different types and subtypes of psychotic disorders are as stated in DSM-IV-TR. (Diagnostic and Statistical Manual of Mental Disorders, 4th ed., American Psychiatric Assoc., Washington, D.C., 2002, p. 297-343).

Schizophrenia as used herein refers to a disorder that lasts for at least 6 months and includes at least one month of active-phase symptoms (i.e., two [or more] of the following: delusions, hallucinations, disorganized speech, grossly disorganized or catatonic behavior, negative symptoms) (Diagnostic and Statistical Manual of Mental Disorders, DSM-IV-TR, 4th ed., American Psychiatric Assoc., Washington, D.C., 2002).

Schizoaffective disorder is defined as a disorder in which a mood episode and the active-phase symptoms of schizophrenia occur together and were preceded or are followed by at least 2 weeks of delusions or hallucinations without prominent mood symptoms (Diagnostic and Statistical Manual of Mental Disorders, DSM-IV-TR, 4th ed., American Psychiatric Assoc., Washington, D.C., 2002).

Schizophreniform disorder is defined as a disorder characterized by a symptomatic presentation that is equivalent to schizophrenia except for its duration (i.e., the disturbance lasts from 1 to 6 months) and the absence of a requirement that there be a decline in functioning (Diagnostic and Statistical Manual of Mental Disorders, DSM-IV-TR, 4th ed., American Psychiatric Assoc., Washington, D.C., 2002).

Schizotypical disorder is defined as a lifetime pattern of social and interpersonal deficits characterized by an inability to form close interpersonal relationships, eccentric behavior, and mild perceptual distortions.

The present invention can be used to treat other psychotic disorders such as delusional disorder; brief psychotic disorder; shared psychotic disorder; substance-induced psychotic disorder, for example psychosis induced by alcohol, amphetamine, cannabis, cocaine, hallucinogens, inhalants, opioids, or phencyclidine; psychotic disorder due to a general medical condition; personality disorder of the paranoid type; personality disorder of the schizoid type; and psychotic disorder not otherwise specified.

For example, treating schizophrenia, schizophreniform, or schizoaffective disorder, as used herein also encompasses treating one or more symptoms (positive, negative, and other associated features) of said disorders, for example treating, delusions, or hallucinations, or any such symptoms associated therewith. Other examples of symptoms of schizophrenia and schizophreniform and schizoaffective disorders include disorganized speech, affective flattening, alogia, anhedonia, inappropriate affect, dysphoric mood (in the form of, for example, depression, anxiety or anger), and some indications of cognitive dysfunction.

Delusional disorder as referred to herein is characterized by at least 1 month of nonbizarre delusions without other active-phase symptoms of schizophrenia. (Diagnostic and Statistical Manual of Mental Disorders, DSM-IV-TR, 4th ed., American Psychiatric Assoc., Washington, D.C., 2002).

Brief psychotic disorder is a disorder that lasts more than 1 day and remits by 1 month. (Diagnostic and Statistical Manual of Mental Disorders, DSM-IV-TR, 4th ed., American Psychiatric Assoc., Washington, D.C., 2002).

Shared psychotic disorder is characterized by the presence of a delusion in an individual who is influenced by someone else who has a longer-standing delusion with similar content. (Diagnostic and Statistical Manual of Mental Disorders, DSM-IV TR, 4th ed., American Psychiatric Assoc., Washington, D.C., 2002).

Psychotic disorder due to a general medical condition is characterized by psychotic symptoms judged to be a direct physiological consequence of a general medical condition. (Diagnostic and Statistical Manual of Mental Disorders, DSM-IV-TR, 4th ed., American Psychiatric Assoc., Washington, D.C., 2002).

Psychotic disorder not otherwise specified is a psychotic presentation that does not meet the criteria for any of the specific psychotic disorders defined in the DSM-IVTR (American Psychiatric Assoc., Washington, D.C., 2002).

In another embodiment, the compounds used in the present invention are useful to treat other disorders that may present with psychotic symptoms as associated features such as dementia of the Alzheimer's type; substance-induced delirium; and major depressive disorder with psychotic features.

In a preferred embodiment, the compounds used in the present invention are useful for treating schizophrenia, a schizoaffective disorder, schizophreniform disorder, or a schizotypical disorder.

The present invention also may be used to treat mood disorders, formerly designated as "affective disorders." Although mood disorders are not a clearly delineated group of illnesses they include unipolar and bipolar depression, generalized anxiety disorder, and more specific anxiety disorders such as agoraphobia, panic disorder and social phobia, obsessive-compulsive disorder and post traumatic stress disorder (PTSD). There is a high level of similarity and co-morbidity between these illnesses and clinicians may consider them as a single group.

The meanings attributed to the different types and subtypes of mood disorders are as stated in DSM-IV-TR under depressive disorders ("unipolar depression") and bipolar disorders, generalized anxiety disorder, and more specific anxiety disorders such as agoraphobia, panic disorder and social phobia, obsessive-compulsive disorder and post traumatic stress disorder (PTSD), the contents of which are incorporated by reference herein. (Diagnostic and Statistical Manual of Mental Disorders", 4th ed., American Psychiatric Assoc., Washington, D.C., 2002, p. 345-484).

The term "affective disorder" as used herein is interchangeable with the term "mood disorders" and refers to disorders that are characterized by changes in mood as the primary clinical manifestation, for example, depression.

The following Examples are provided to illustrate various aspects of the invention and should not be construed as limiting the invention in any manner.

EXAMPLES

Dysfunctions of sensory gating and information processing have been putatively associated with clinical features such as perpetual aberrations, hallucinations and distraction and been considered as potential precursors of sensory overload, cognitive fragmentation and disorganization. Among the physiological measures, one approach has involved the startle reflex with the prepulse inhibition (PPI) paradigm. Patients with schizophrenia exhibit deficits in prepulse inhibition (PPI) of startle, which is linked to both positive and negative symptoms. PPI refers to a reduction in the acoustic startle reflex to a loud noise when the loud noise is preceded by a weak auditory stimulus. At short lead intervals, this has the effect of markedly reducing or gating the amplitude of the startle response and increasing its latency. Disruption of PPI occurs with agonists of dopamine and serotonin, and with glutamate/N-methyl D aspartate (NMDA) receptor antagonists, or can be induced by genetic (e.g., DBA2 mouse strain) and experimental manipulations (e.g., rearing rats in isolation, neurotoxic lesions, or other methods). The naturally occurring deficit in PPI in the DBA2 mouse strain has been shown to be an effective model to evaluate antipsychotic agents and increases in baseline PPI has been observed with clinically effective antipsychotics such as haloperidol, risperidone, and clozapine. (Olivier B., et al., Psychopharmacology (2001) vol. 156:284-290; Ouagazzal A-M., Psychopharmacology (2001) vol. 156:273-283; Simosky J. K., Psychopharmacology (2003) vol. 165:386-396).

Example 1

Effects of Compound A in Mouse Prepulse Inhibition Model

Figure 1:
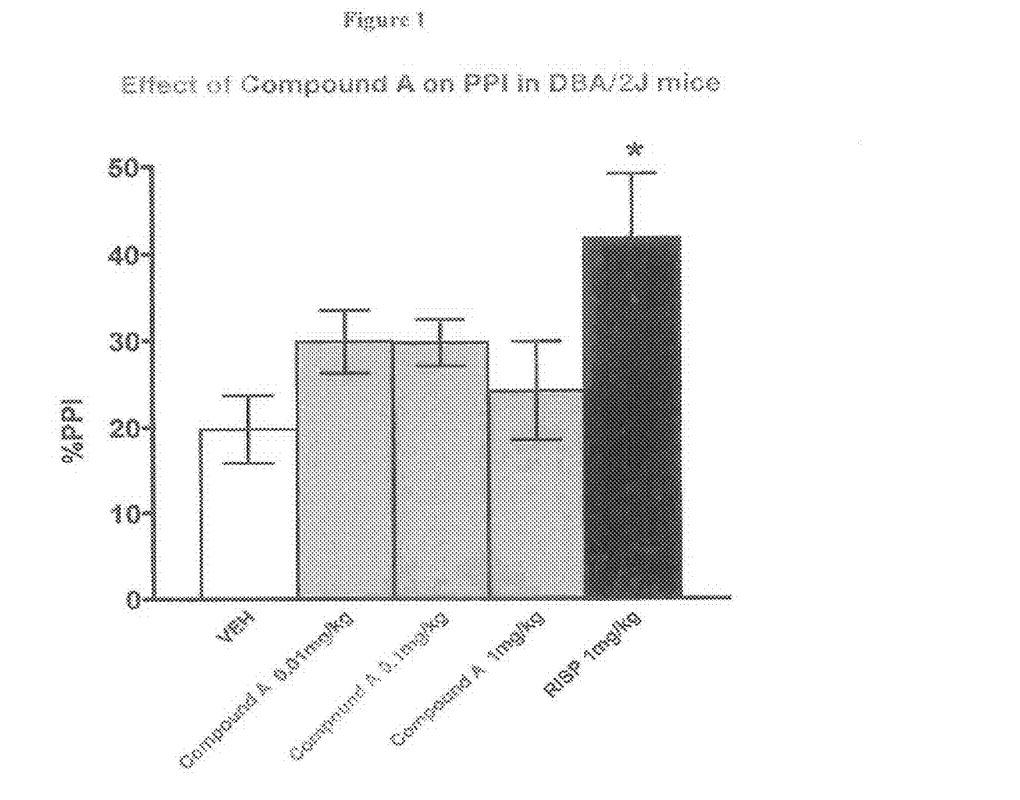
FIG. 1 graphically represents the effects of 2-{4'-[(3aR, 6aR)-5-methylhexahydropyrrolo[3,4-b]pyrrol-1(2H)-yl]-1, 1'-biphenyl-4-yl}pyridazin-3(2H)-one (Compound A) administered in 0.01, 0.1, and 1 mg/kg doses intraperitoneally (i.p.), 30 minutes before testing for prepulse inhibition DBA2/J mice. Risperidone, a representative antipsychotic drug, was used as a positive control in the study.

The PPI model was used to investigate the effect of 2-{4'-[(3aR,6aR)-5-methylhexahydropyrrolo[3,4-b]pyrrol-1(2H)-yl]-1,1'-biphenyl-4-yl}pyridazin-3(2H)-one (Compound A). Animals: Male DBA/2J mice (Jackson Labs AX9 facility, Bar Harbor, Me., USA) at age 6-8 weeks old were used. They were housed under standard facility conditions in groups of eight on a 12 h light/dark cycle (lights on at 0600 h) with ad libitum access to food and water.
Chemicals: 2-{4'-[(3aR,6aR)-5-Methylhexahydropyrrolo[3,4-b]pyrrol-1(2H)-yl]-1,1'-biphenyl-4-yl}pyridazin-3(2H)-one was prepared at Abbott Laboratories; risperidone (3-[2-[4-(6-fluoro-1,2-benzisoxazol-3-yl)-1-piperidinyl]ethyl]-6,7,8,9-tetrahydro-2-methyl-4H-pyridol[1,2-a]pyrimidin-4-one, MW 410.5) was obtained from ICN Biomedicals Inc. (Aurora, Ohio, USA).
Preparation of Compounds: Compound A was dissolved in a solution containing ½ the final volume and citric acid (1.1× the mg amount of Compound A), pH~5.0-5.3 with 1 N NaOH, and brought to full volume], and dosed intraperitoneally (10 ml/kg) 30 min prior to testing.
Experimental Procedure: Startle response and PPI were measured using startle chambers from Hamilton Kinder (Poway, Calif., USA). Each chamber contained a plexiglas rectangle with an adjustable ceiling housed in a ventilated sound-attenuated cubicle. The ceiling was adjusted on an individual (animal by animal) basis to allow for adequate headroom but no rears or extensive locomotion. The chamber was placed over an anchor plate attached to a piezoelectric disk to transduce startle responses to a computer. A loudspeaker located in each chamber delivered the background noise (65 dB) and the acoustic stimuli. A constant white noise was maintained in the experimental room for the duration of the experiment by a white noise generator (Radio Shack, USA). Each session was initiated with a 5-minute acclimation period followed by four successive 120 dB, 40 ms trials. These trials were not included in the main analysis, but are referred to as baseline responses. Animals were then presented with 5 different trial types. Startle pulse (120 dB, 40 ms), or prepulse stimulus of one of three sound levels (70, 75, or 80 dB) for 20 ms, followed 100 ms later by an acoustic startle (120 dB) for 40 ms, or no stimulus at all. A total of 12 trials under each condition were delivered in a random sequence and all trials were separated by a variable inter-trial interval of 5-25 s. Finally, this sequence ended with the presentation of four 120 dB, 40 ms sound bursts (not included in the main analyses, but included in the baseline or habituation analyses). The animals were injected with the test compounds 30 minutes before the start of the trials. In the startle alone trials, the amount of PPI was calculated as a percentage score for each acoustic prepulse trial type using (typically) the formula: [(startle response for prepulse+pulse)/(startle response for pulse alone)]*100.
Statistics: Data were analyzed using a one-way ANOVA. All post hoc significance was determined using Dunnett's multiple comparison test (p<0.05 was regarded as significance). Results: As shown in FIG. 1, Compound A alone at doses of 0.01, 0.1 and 1.0 mg/kg did not significantly alter PPI responding.

Example 2

Figure 2:
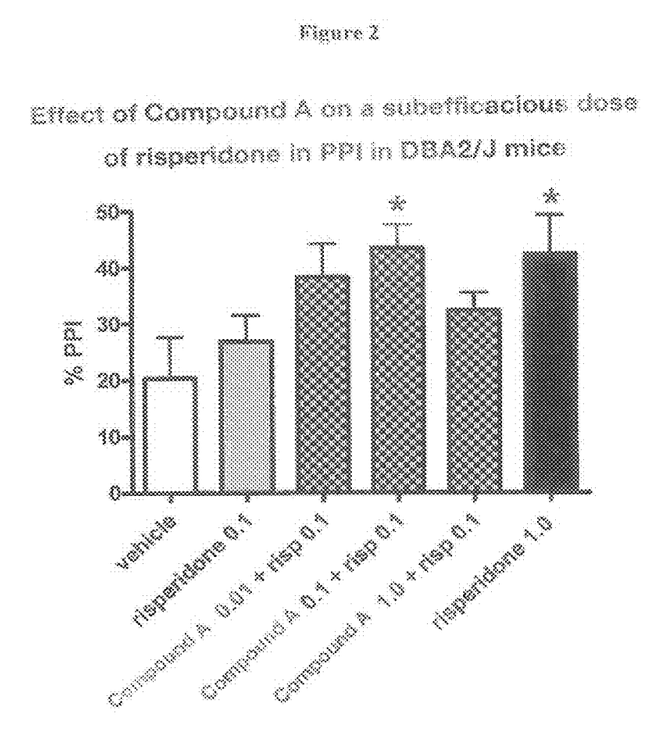
FIG. 2 graphically represents the effects of Compound A on a subefficacious dose of risperidone in the prepulse inhibition model in DBA2/J mice. Compound A was administered in 0.01, 0.1, and 1 mg/kg doses intraperitoneally 10 minutes before the administration of 0.1 mg/kg i.p. risperidone. Prepulse inhibition testing began 25 minutes after risperidone treatment.

Compound A, an $H_3$ Antagonist, Potentiated the Antipsychotic Effect of Risperidone The PPI model was used to investigate the effect of 2-{4'-[(3aR,6aR)-5-methylhexahydropyrrolo[3,4-b]pyrrol-1(2H)-yl]-1,1'-biphenyl-4-yl}pyridazin-3(2H)-one (Compound A) (0.01-1.0 mg/kg) on a subefficacious dose of risperidone. The methods used were the same as those described above in Example 1, except Compound A (0.01, 0.1, or 1.0 m/kg, i.p.) was dosed 35 minutes prior to testing, and risperidone (0.1 or 1 mg/kg) was dosed 25 minutes prior to testing.
Statistics: Data were analyzed using a one-way ANOVA. All post hoc significance was determined using Dunnett's multiple comparison test (p<0.05 was regarded as significance). Results: As shown in FIG. 2, risperidone (0.1 mg/kg) was found to be more efficacious in the presence of Compound A and attained maximal efficacy (comparable to that observed by 1.0 mg/kg risperidone) in combination with 0.1 mg/kg Compound A. This demonstrates that a dose of an antipsychotic that is normally weakly efficacious can be made to exhibit robust efficacy with concomitant $H_3$ antagonism.

Example 3

The $H_3$ Antagonist Compound A does not Exacerbate the Cataleptic Effect of Risperidone Animals: Male Sprague Dawley rats (CRL: CD (SD), Charles River Laboratories, Omaha, Nebr., USA) weighing 300-325 g were used for the experiment. They were housed under standard conditions in groups of 4 rats on a 12 h light/dark cycle (lights on at 0600 h) with ad libitum access to food and water.
Preparation of Compounds: 2-{4'-[(3aR,6aR)-5-Methylhexahydropyrrolo[3,4-b]pyrrol-1(2H)-yl]-1,1'-biphenyl-4-yl}pyridazin-3(2H)-one (Compound A) and risperidone were solubilized as described above, and were administered in solution in a volume of 1.0 ml/kg body weight.
Experimental Procedure: Rats were handled and habituated to the testing room before starting. On test day rats were transferred into individual cages and left undisturbed for at least one hour. All compounds were dosed at 1.0 ml/kg i.p. In the case of co-treatment, the $H_3$ antagonist was administered 10 minutes prior to the risperidone. Rats were tested at 60, 120, 180, and 240 minutes post-injection for cataleptic responses and returned to cages in-between test sessions. The degree of catalepsy was measured by gently placing both forepaws over a metal bar (1.1 cm. diameter suspended 8 cm. above the table top). The time in seconds until the rat took both paws off the bar was recorded, with a maximum cut-off of 300 seconds. The total duration of catalepsy in the different time points was used for analysis. At least 5 trials were attempted on each rat with 5 seconds used as a low-end cut-off for catalepsy (time scored as zero). For catalepsy times between 5-15 seconds, the highest time of 5 trials was recorded. Alternately, any catalepsy trial time that was greater than 15 seconds (up to 300 seconds) was recorded.

Statistics: Data for the 4 times points were summed across the session, and the total catalepsy scores were analyzed using a one-way analysis of variance (ANOVA). All post hoc significance was determined using Dunnett's multiple comparison test ($p<0.05$ was regarded as significance).

Figure 3:
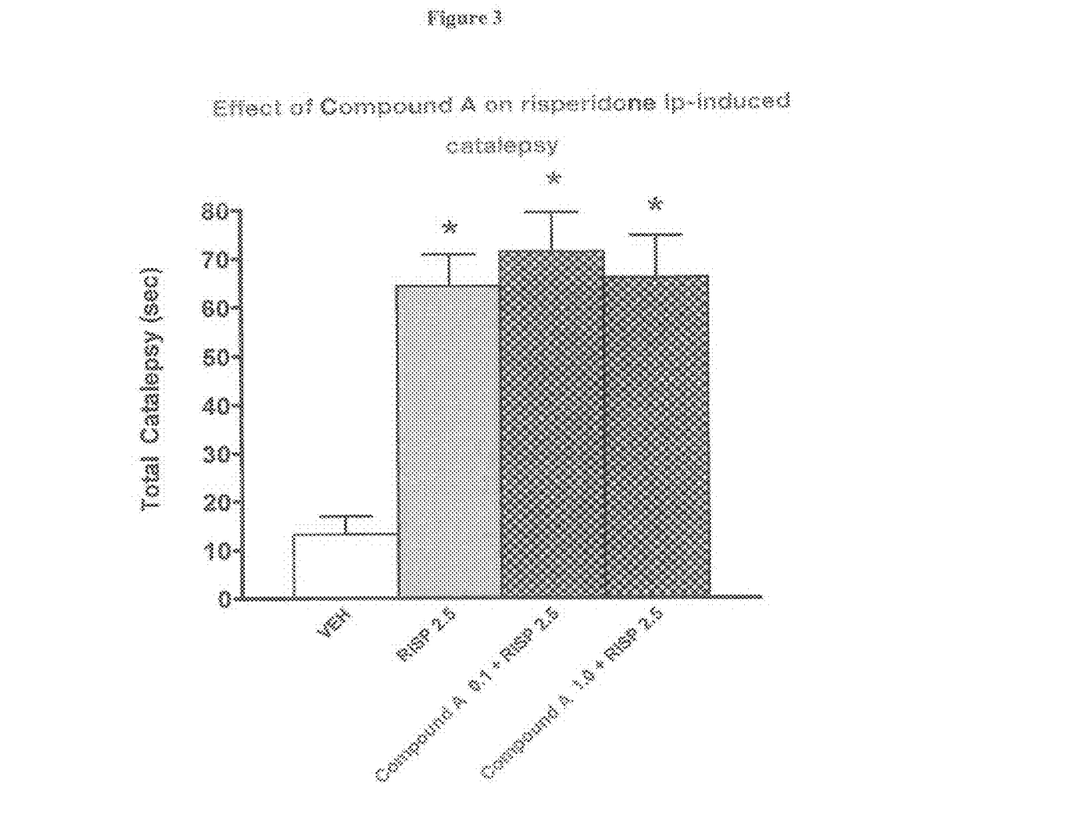
FIG. 3 graphically represents the effect of Compound A on catalepsy, a drug-induced side effect associated with risperidone use. Compound A was administered intraperitoneally in 0.1 and 1.0 mg/kg doses together with 0.1 mg/kg ip dose of risperidone 60 minutes before commencement of catalepsy testing.

Results: As shown in FIG. 3, Compound A (0.1 or 1.0 mg/kg i.p.) did not significantly alter cataleptic behavior of risperidone (2.5 mg/kg i.p.), when administered in combination. The study demonstrates that histamine $H_3$ antagonists do not alter the side effect profile of the antipsychotic drug.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A method for treating a psychotic disorder in a patient, in need thereof comprising:
   (i) administering an amount of antipsychotic therapeutic agent to the patient; and
   (ii) administering an amount of histamine $H_3$ antagonist; to said patient in need of treatment for a psychotic disorder; wherein the histamine $H_3$ receptor antagonist is a compound of formula:

(I)

or a pharmaceutically acceptable salt thereof, wherein:
   $R_1$ is alkyl, $C_3$-$C_5$ cycloalkyl, or ($C_3$-$C_5$ cycloalkyl)methyl;
   $R_{2a}$, $R_{2b}$, $R_{2c}$, $R_{2d}$, $R_{2e}$, and $R_{2f}$ each are independently hydrogen, methyl, or fluoromethyl;
   $R_{3a}$, $R_{3b}$, $R_{3c}$, and $R_{3d}$ are each independently hydrogen, alkyl, fluoroalkyl, fluoroalkoxy, alkoxy, thioalkoxy, halogen, or nitrile, with the proviso that when one or more of $R_{3a}$, $R_{3b}$, $R_{3c}$, and $R_{3d}$ are alkyl, then at least one of $R_{3a}$, $R_{3b}$, $R_{3c}$, and $R_{3d}$ is fluoroalkyl, fluoroalkoxy, alkoxy, thioalkoxy, halogen, or nitrile;
   $L_1$ is a bond, oxygen, sulfur, carbonyl, alkylene, alkylcarbonyl, alkylamino, —C(=N-Oalkyl)-, $NR_4$, —C(=O)$NR_4$—, or —$NR_4$C(=O)—;
   $L_2$ is a bond, oxygen, sulfur, carbonyl, alkylene, alkylcarbonyl, alkylamino, —C(=N-Oalkyl)-, $NR_5$, —C(=O)$NR_5$—, or —$NR_5$C(=O)—;
   $Cy_1$ is aryl, cycloalkyl, cycloalkenyl, heteroaryl, or heterocycle;
   $Cy_2$ is aryl, cycloalkyl, cycloalkenyl, heteroaryl or heterocycle, wherein the heteroaryl or heterocycle moiety has 1, 2, or 3 heteroatoms selected from nitrogen, oxygen, and sulfur, provided that at least one heteroatom is nitrogen; and
   $R_4$ and $R_5$ at each occurrence is hydrogen or alkyl; provided that $Cy_2$ is not 2. The method of claim 1, wherein the amounts of (i) and (ii) together are effective in treating a psychotic disorder.

3. The method of claim 1, wherein $L_1$ is a bond; $L_2$ is a bond; $R_{3a}$, $R_{3b}$, $R_{3c}$, and $R_{3d}$ are all hydrogen; $Cy_1$ is phenyl, and $Cy_2$ is aryl, cycloalkyl, cycloalkenyl, heteroaryl or heterocycle, wherein the heteroaryl or heterocycle moiety has 1, 2, or 3 heteroatoms selected from nitrogen, oxygen, and sulfur, provided that at least one heteroatom is nitrogen.

4. The method of claim 3, wherein $Cy_2$ is pyridazinone.

5. The method of claim 1, wherein the histamine $H_3$ receptor antagonist is 2-{4'-[(3aR,6aR)-5-methylhexahydropyrrolo[3,4-b]pyrrol-1(2H)-yl]-1,1'-biphenyl-4-yl}pyridazin-3(2H)-one.

6. The method of claim 1, wherein the histamine $H_3$ receptor antagonist is 2-{5-[4-((3aR,6aR)-5-methyl-hexahydropyrrolo[3,4-b]pyrrol-1-yl)-phenyl]-pyridin-2-yl}-2H-pyridazin-3-one.

7. The method of claim 2, wherein the amount of (ii) is a sub efficacious amount.

* * * * *